(12) United States Patent
Divo et al.

(10) Patent No.: US 9,545,202 B2
(45) Date of Patent: Jan. 17, 2017

(54) DEVICE AND METHOD FOR MEASURING OBJECTIVE OCULAR REFRACTION AND AT LEAST ONE GEOMETRIC-MORPHOLOGICAL PARAMETER OF AN INDIVIDUAL

(71) Applicant: ESSILOR INTERNATIONAL (COMPAGNIE GENERALE D'OPTIQUE), Charenton le Pont (FR)

(72) Inventors: Fabien Divo, Charenton-le-Pont (FR); Guilhem Escalier, Charenton-le-Pont (FR)

(73) Assignee: ESSILOR INTERNATIONAL (COMPAGNIE GENERALE D'OPTIQUE), Charenton-le-Pont (FR)

( * ) Notice: Subject to any disclaimer, the term of this patent is extended or adjusted under 35 U.S.C. 154(b) by 191 days.

(21) Appl. No.: 14/411,522

(22) PCT Filed: Jul. 4, 2013

(86) PCT No.: PCT/FR2013/051595
§ 371 (c)(1),
(2) Date: Dec. 29, 2014

(87) PCT Pub. No.: WO2014/006341
PCT Pub. Date: Jan. 9, 2014

(65) Prior Publication Data
US 2015/0146168 A1    May 28, 2015

(30) Foreign Application Priority Data

Jul. 6, 2012   (FR) ..................... 12 01925

(51) Int. Cl.
*A61B 3/14*   (2006.01)
*A61B 3/18*   (2006.01)
(Continued)

(52) U.S. Cl.
CPC ............... *A61B 3/18* (2013.01); *A61B 3/0008* (2013.01); *A61B 3/0025* (2013.01);
(Continued)

(58) Field of Classification Search
CPC ... A61B 3/0008; A61B 3/0025; A61B 3/0075; A61B 3/0083; A61B 3/0091; A61B 3/028; A61B 3/032; A61B 3/08; A61B 3/11; A61B 3/111; A61B 3/113; A61B 3/15; A61B 3/152; A61B 3/158; A61B 3/18; A61B 3/185; G02C 7/027; G02C 7/028; G02C 13/005
(Continued)

(56) References Cited

U.S. PATENT DOCUMENTS

| 8,708,490 B2 * | 4/2014 | Baranton ................. A61B 3/14 348/78 |
| 2003/0081173 A1 | 5/2003 | Dreher |
| 2006/0290885 A1 | 12/2006 | Covannon et al. |

FOREIGN PATENT DOCUMENTS

| EP | 0 498 363 A1 | 8/1992 |
| WO | 2011/058244 A1 | 5/2011 |

OTHER PUBLICATIONS

International Search Report, dated Oct. 9, 2013, from corresponding PCT application.

* cited by examiner

*Primary Examiner* — Huy K Mai
(74) *Attorney, Agent, or Firm* — Young & Thompson

(57) ABSTRACT

Disclosed is a device for measuring ocular refraction and a geometric-morphological parameter of an individual, including: a gaze-stimulating target placed so as to stimulate the gaze of the individual in a posture associated with a proximity value and a sight axis; an illuminating system able to generate at least one illuminating beam in the direction of
(Continued)

the eyes of the individual; an image-capturing system; and a computer able to receive at least one first image captured by the image-capturing system. According to the invention, the image-capturing system is able to acquire an image of part of the face surrounding the eyes of the individual, and the computer is able to extract, from the acquired image, a first measurement of a glazing parameter and a first measurement of objective ocular refraction by refraction of the illuminating beam on the eyes of the individual in the given posture.

23 Claims, 6 Drawing Sheets

(51) Int. Cl.
*A61B 3/00* (2006.01)
*A61B 3/028* (2006.01)
*A61B 3/113* (2006.01)
*A61B 3/103* (2006.01)
*G02B 27/10* (2006.01)
*G02C 13/00* (2006.01)

(52) U.S. Cl.
CPC ............ *A61B 3/0091* (2013.01); *A61B 3/028* (2013.01); *A61B 3/103* (2013.01); *A61B 3/113* (2013.01); *A61B 3/14* (2013.01); *G02B 27/10* (2013.01); *G02C 13/003* (2013.01); *G02C 13/005* (2013.01)

(58) Field of Classification Search
USPC ............... 351/204, 205, 209, 221, 222, 237, 240,351/245, 246, 159.74–159.76, 178
See application file for complete search history.

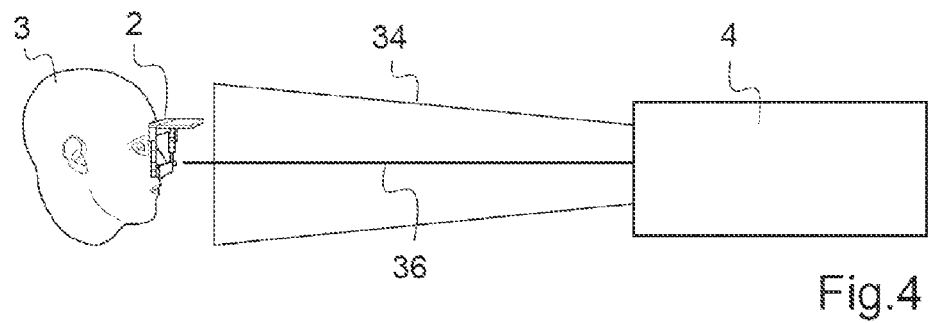
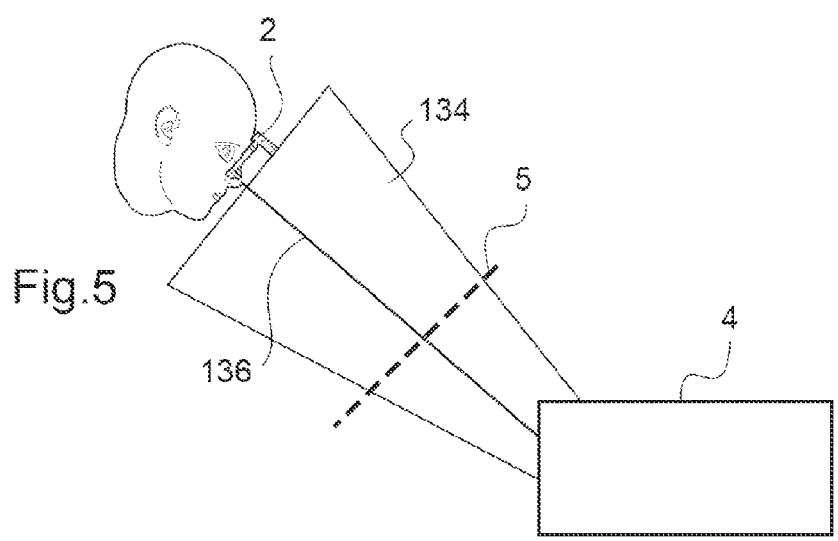
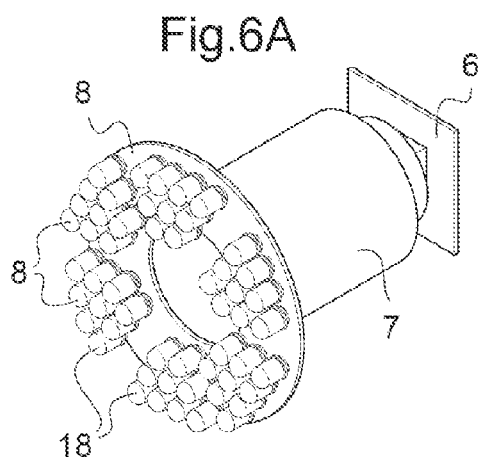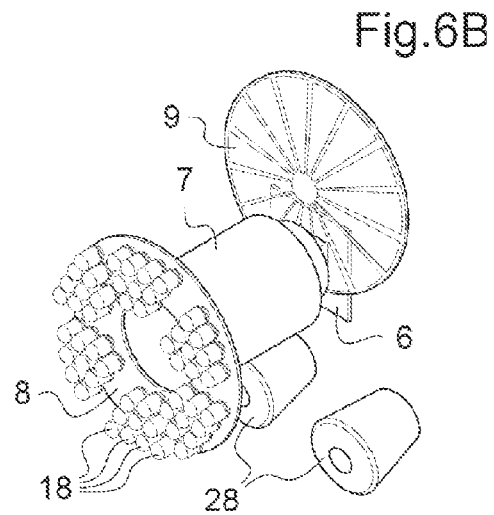

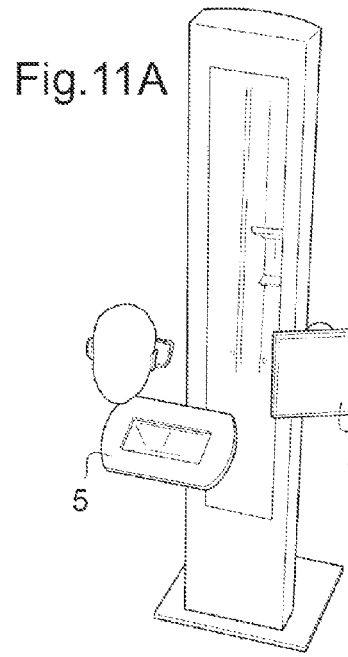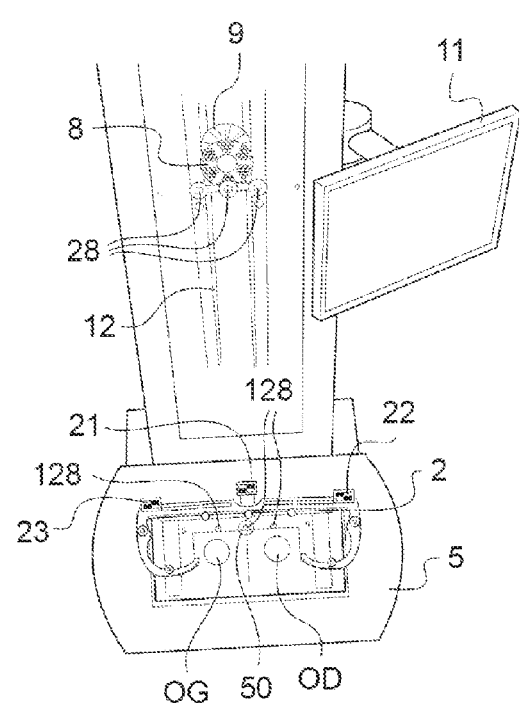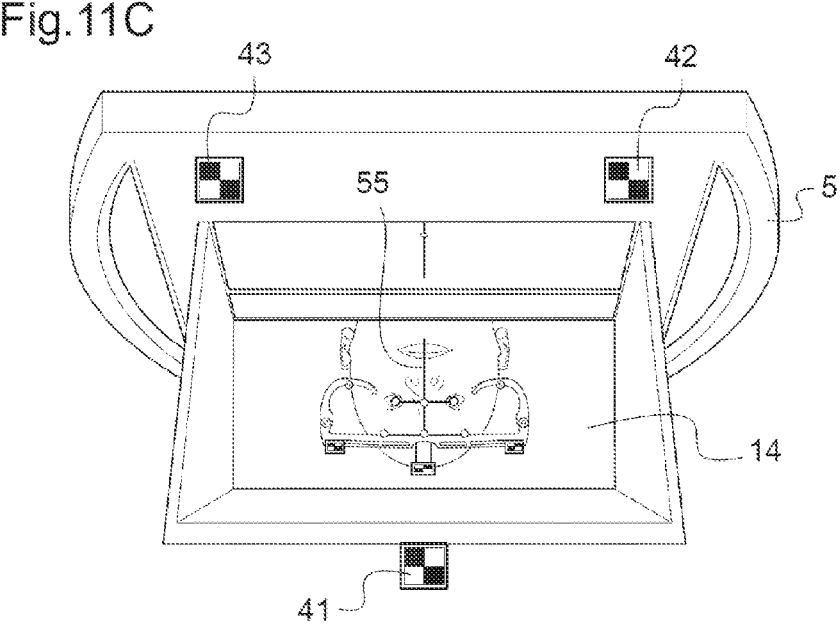

DEVICE AND METHOD FOR MEASURING OBJECTIVE OCULAR REFRACTION AND AT LEAST ONE GEOMETRIC-MORPHOLOGICAL PARAMETER OF AN INDIVIDUAL

TECHNICAL FIELD OF THE INVENTION

The present invention relates generally to the field of measurement apparatuses for the manufacture of spectacles for visual correction.

It relates more particularly to an apparatus allowing simultaneous measurement of a geometrico-morphological parameter and of an ocular refraction parameter in one or more visual behaviors of the spectacles wearer, for example in far vision (FV) and in near vision (NV). More precisely, the invention relates to an apparatus allowing the measurement of frame-fitting parameters and of ocular refraction parameters of an individual.

PRIOR ART

Today it is necessary to implement separate apparatuses to determine on the one hand ocular refraction parameters and on the other hand geometrico-morphological parameters and especially frame-fitting parameters. In the commonly widespread language of the art of ophthalmic optics, the expression "geometrico-morphological" parameter of an individual is intended to mean a geometric or morphological parameter relating to the wearer's face such as the interpupillary distance, the head angle (roll, pitch, yaw) with respect to a vertical line in a determined posture. The expression "frame-fitting parameter" is intended to mean a geometric or physionomic parameter relating to the wearer's face and/or to the spectacles frame such as: the height of the eyes with respect to the lower edge of a selected frame, the vertex (distance between the eye and the inner surface of the spectacles lens), the frame wrap angle, the frame pantoscopic angle.

On the one hand, the measurement of the ocular refraction is performed by means of on-table instruments. Ocular refraction is generally measured in a subjective manner at the practitioner's and verified at the optician's in monocular in an objective manner. FIG. 1 illustrates a screen making it possible to display measurement results for the ocular refraction parameters, the measurement being performed without correction spectacles. The screen displays, superimposed on an image of the subject's face, a rectangular framing reference 20 and a measurement of the interpupillary distance (IPD). The same screen can represent the measurements of ocular refraction for the right eye (RE) and for the left eye (LE) respectively. The graphical interface can for example display the numerical results of measuring refraction parameters, asymmetry of gaze, pupil diameter and IPD.

On the other hand, an apparatus in the form of a column or tablet is generally used to determine the frame-fitting parameters. FIG. 2 illustrates an image of an individual wearing a frame 1 on which is fixed a clip 2 furnished with markers 21, 22, 23, 24. An image processing makes it possible to determine the personalized frame-fitting parameters such as: height of the gaze (H) with respect to the lower edge of the frame, pantoscopic angle of the frame, etc. The graphical interface represented in FIG. 2 can also indicate results of measuring the frame-fitting parameters such as: the relative position of each eye with respect to the lens considered, as well as the visual behavior of the individual during the measurement, for example the inclination of their head.

The various steps of taking measurements of the ocular refraction and frame-fitting parameters require the wearer to move and to be confronted with at least two different instruments. For the optician, the succession of these two important measurement steps takes time. Moreover, the measurement of the frame-fitting parameters is generally performed in a single posture of the subject and a single position of vision, the wearers head being straight and the subject looking straight ahead. The measurement of the frame-fitting parameters does not generally take into account the various postures of the subject and/or various vision conditions. Moreover, certain instruments demand the use of a chinstrap and/or of a frontal rest in order to determine the head posture and the vision conditions of the wearer. These instruments impose posture constraints on the wearer and do not provide any measurement under natural conditions of posture and vision, with no contact constraint.

SUBJECT OF THE INVENTION

In order to remedy the aforementioned drawbacks of the prior art, the present invention proposes to combine the taking of measurements of the geometrico-morphological (especially frame-fitting) parameters with the measurement of ocular refraction for various positions of the gaze and various proximity values.

More particularly, there is proposed according to the invention a device for measuring objective ocular refraction and at least one geometrico-morphological parameter of an individual, said device comprising: at least one first target for stimulating the gaze having a center disposed in a first position so as to stimulate the gaze of the individual in a first posture associated with a first proximity value and a first sighting axis, a lighting system comprising at least one luminous source, the lighting system being able to generate at least one lighting beam directed toward the eyes of the individual in the first posture, an image capture system and a computer.

According to the invention, the measuring device furthermore comprises at least one second target for stimulating the gaze having a center disposed in a second position so as to stimulate the gaze of the individual in a second posture associated with a second proximity value and a second sighting axis, and an optical return system disposed between on the one hand the second target for stimulating the gaze and on the other hand the image capture system and the lighting system, the optical return system being able, in a determined orientation, to return the lighting beam toward the eyes of the individual looking at the second target in a second posture, and the image capture system is adapted for obtaining a first image acquisition comprising a part of the face surrounding the eyes of the individual in the first posture, and the image capture system is adapted for obtaining via the optical return system a second image acquisition comprising a part of the face surrounding the eyes of the individual in the second posture, and the computer is adapted for receiving and extracting from said first image on the one hand a first measurement of at least one geometrico-morphological parameter of the individual in the first posture and on the other hand a first measurement of objective ocular refraction by refraction of the lighting beam on the eyes of the individual in the first posture, and the computer is adapted for extracting from said second image acquisition on the one hand a second measurement of a geometrico-morphological parameter of the individual in the second posture and on the other hand a second measurement of objective ocular refraction by refraction of the lighting beam on the eyes of the individual in the second posture.

The device thus allows a measurement of objective ocular refraction and of at least one geometrico-morphological parameter of an individual in one and the same determined posture.

The values thus measured of these two magnitudes (ocular refraction on the one hand and geometrico-morphological parameter(s) on the other hand) can then be recorded and utilized subsequently.

Preferably, said at least one geometrico-morphological parameter consists of at least one frame-fitting parameter for an individual wearing a spectacles frame.

Other nonlimiting and advantageous characteristics of a measuring device in accordance with the invention are as follows:
the lighting system generates a lighting beam and the image capture system defines an optical axis, the lighting system and the image capture system are disposed with respect to one another in such a way that the lighting beam is centered on the optical axis of the image capture system.

In an advantageous manner, the measuring device furthermore comprises:
means for measuring the optical distance between said image capture system and the individual in the first posture and/or in the second posture, said distance measuring means being selected in a nonlimiting manner from among: a telemeter, an image processing system based on the image quality, an image processing system based on a measurement of markers of a clip fixed to a spectacles frame, a calibration system or a system for measuring distance by ultrasounds;
the measuring device furthermore comprises a clip furnished with markers which is intended to be mounted on a spectacles frame and the image capture system exhibits an image field adapted for simultaneously detecting an image comprising a part of the face surrounding the eyes of the individual wearing the spectacles frame and an image of the markers of the clip mounted on the spectacles frame;
the lighting system comprises at least one infrared luminous source and image capture system comprises an infrared camera;
means of displacement and/or of orientation of the image capture system which are able to align the optical axis of the image capture system with the first ocular sighting axis associated with the first target and/or respectively with the second ocular sighting axis associated with the second target; and/or
means of displacement and/or of orientation of the optical return system which are able to return the optical axis of the image capture system to the first ocular sighting axis associated with the first target and respectively to the second ocular sighting axis associated with the second target.

Advantageously, the measuring device comprises a column supporting the lighting system, the image capture system, the computer, at least one first target and a viewing screen.

The invention also proposes a method for measuring objective ocular refraction and at least one geometrico-morphological parameter of an individual, said method comprising the following steps:
activating at least one first target for stimulating the gaze so as to stimulate the gaze of the individual in a first posture associated with a first proximity value and a first sighting axis,
generating at least one lighting beam directed toward the eyes of the individual in the first posture,
obtaining at least one first image acquisition of a part of the face surrounding the eyes of the individual,
computing on the basis of said at least one first image acquisition on the one hand a first measurement of at least one geometrico-morphological parameter of the individual in the first posture and on the other hand a first measurement of objective ocular refraction of the individual in the first posture.

In an advantageous manner, the measuring method furthermore comprises the following steps:
activating at least one second target for stimulating the gaze so as to stimulate the gaze of the individual in a second posture associated with a second proximity value and a second sighting axis,
generating at least one lighting beam directed toward the eyes of the individual in the second posture,
obtaining at least one second image acquisition of a part of the face surrounding the eyes of the individual,
computing on the basis of said at least one second image acquisition on the one hand a second measurement of at least one geometrico-morphological parameter of the individual in the second posture and on the other hand a second measurement of objective ocular refraction of the individual in the second posture.

Preferably, said at least one geometrico-morphological parameter consists of at least one frame-fitting parameter for an individual wearing a spectacles frame, the frame-fitting parameter being selected from among the interpupillary distances, the lens-eye distance (DLE), the position of the center of rotation of the eye (CRE), the height (H) of the eyes in relation to the lower edge of the frame.

According to a particular embodiment, the first measurement of at least one geometrico-morphological parameter and the first measurement of objective ocular refraction of the individual in the first posture are sequential measurements, or, respectively, the second measurement of at least one geometrico-morphological parameter and the second measurement of objective ocular refraction of the individual in the second posture are sequential measurements.

Alternatively, the first measurement of at least one geometrico-morphological parameter and the first measurement of objective ocular refraction of the individual in the first posture are simultaneous measurements and respectively the second measurement of at least one geometrico-morphological parameter and the second measurement of objective ocular refraction of the individual in the second posture are simultaneous measurements.

In a particular embodiment, the measuring method comprises an additional step of controlling the first posture and/or the second posture in such a way that the first sighting axis associated with the first posture and/or respectively the second sighting axis associated with the second posture, is included in a cone centered on the optical axis of the image capture system, said cone having a vertex angle of less than or equal to ten degrees.

Advantageously, the measuring method furthermore comprises a step of measuring an angle of lowering of the gaze of the individual.

In a particular embodiment, the measuring method furthermore comprises a step of measuring at least one physiological parameter of vision of the individual wearing a spectacles frame in the first and/or second posture, the physiological vision parameter being representative of strabismus, keratoconus or of cataracts or of behavioral parameters of the individual. The behavioral parameters relate especially to parameters known to the person skilled in the art such as the eye/head coefficient, laterality, eye cap/head cap.

In another particular embodiment, the individual wearing a spectacles frame equipped with lenses, the method comprises an additional step of correcting the ocular refraction measurement on the basis of at least one of the following values: the power correction value of the lenses or the value of the transmission coefficient of the lenses.

In another particular embodiment, the measuring method furthermore comprises a step of measuring an angle of lowering of the gaze of the individual wearing a spectacles frame, or else a step of measuring an angle of roll, of pitch, and/or of yaw of the head in relation to a vertical axis on the basis of the information of the clip for example.

DETAILED DESCRIPTION OF AN EXAMPLE EMBODIMENT

The description which follows with regard to the appended drawings, given by way of nonlimiting examples, will clearly elucidate the gist of the invention and how it may be embodied.

In the appended drawings:

FIG. 4 represents schematically in side view a measurement apparatus according to an embodiment of the invention under far vision measurement conditions;

Figure 7A:
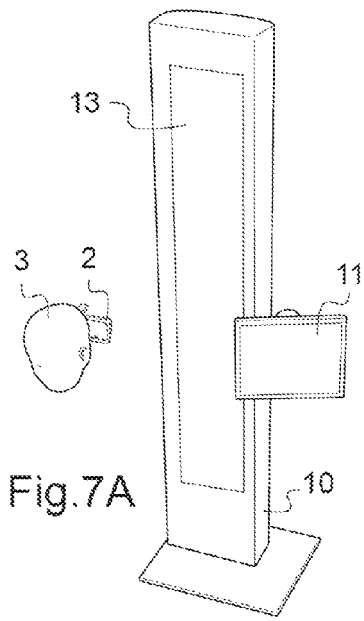
Figure 7B:
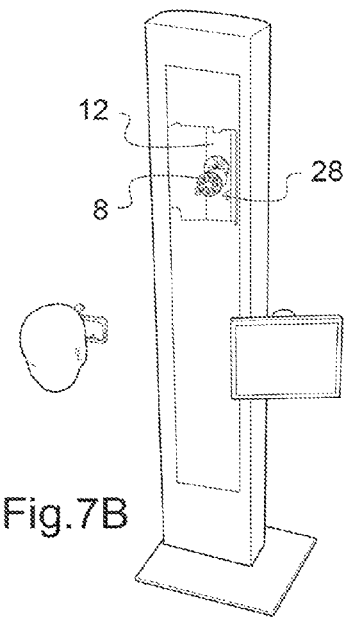
Figure 8A:
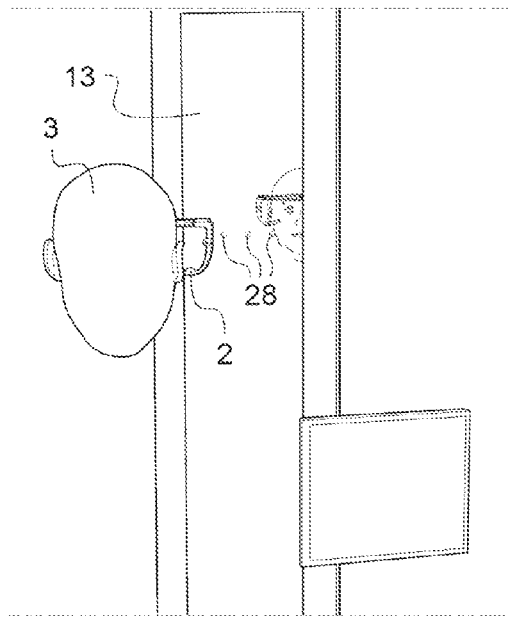
Figure 8B:
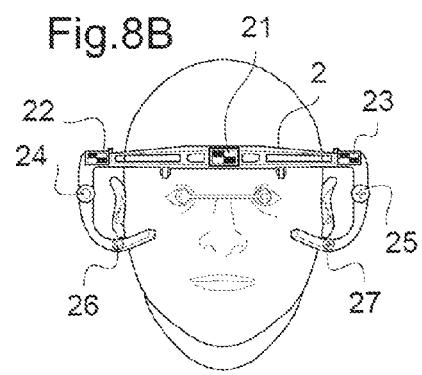
Figure 8C:
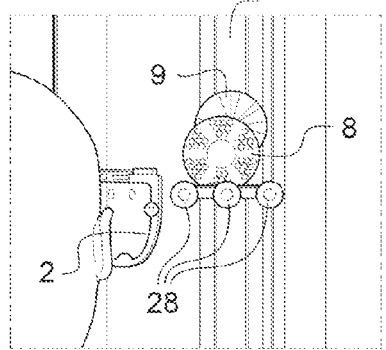
Figure 9:
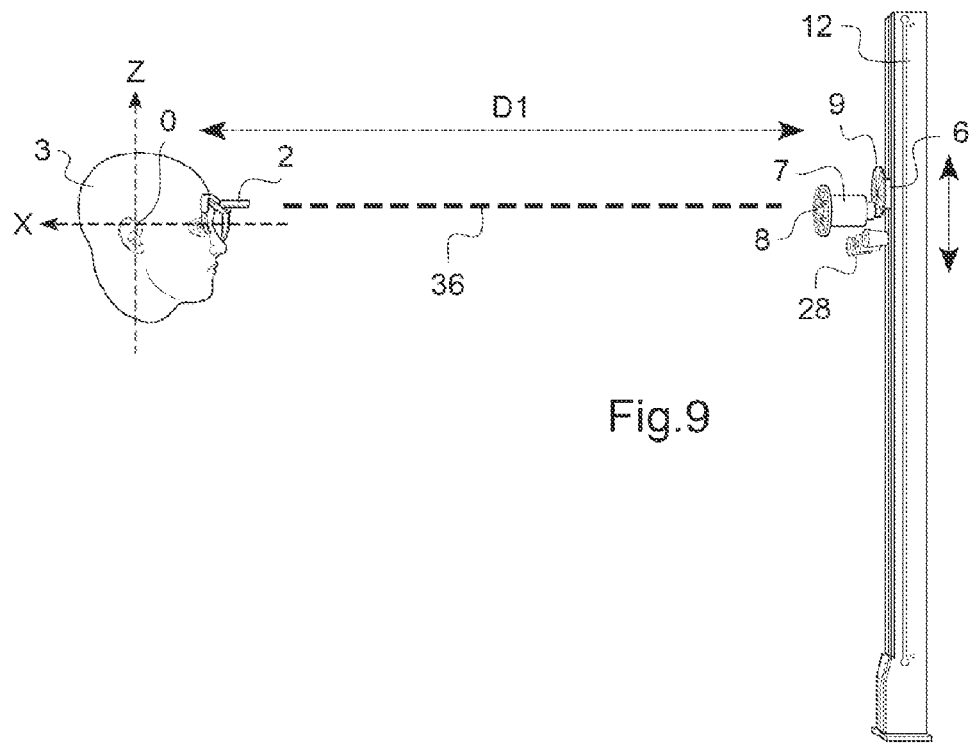
Figure 10:
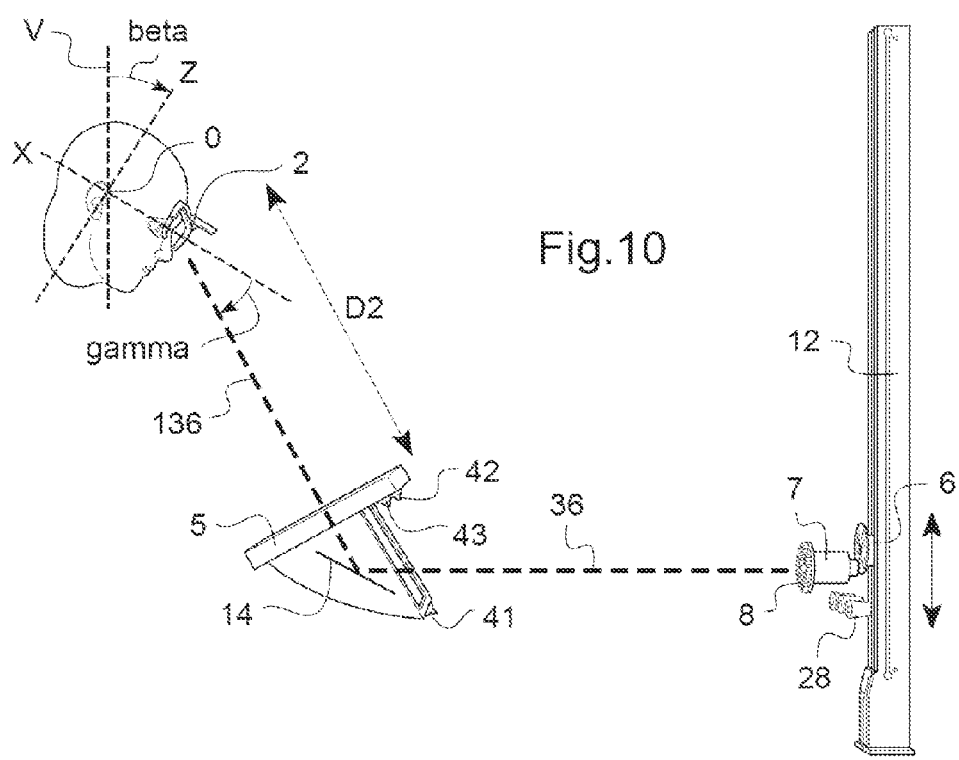
Figure 12:
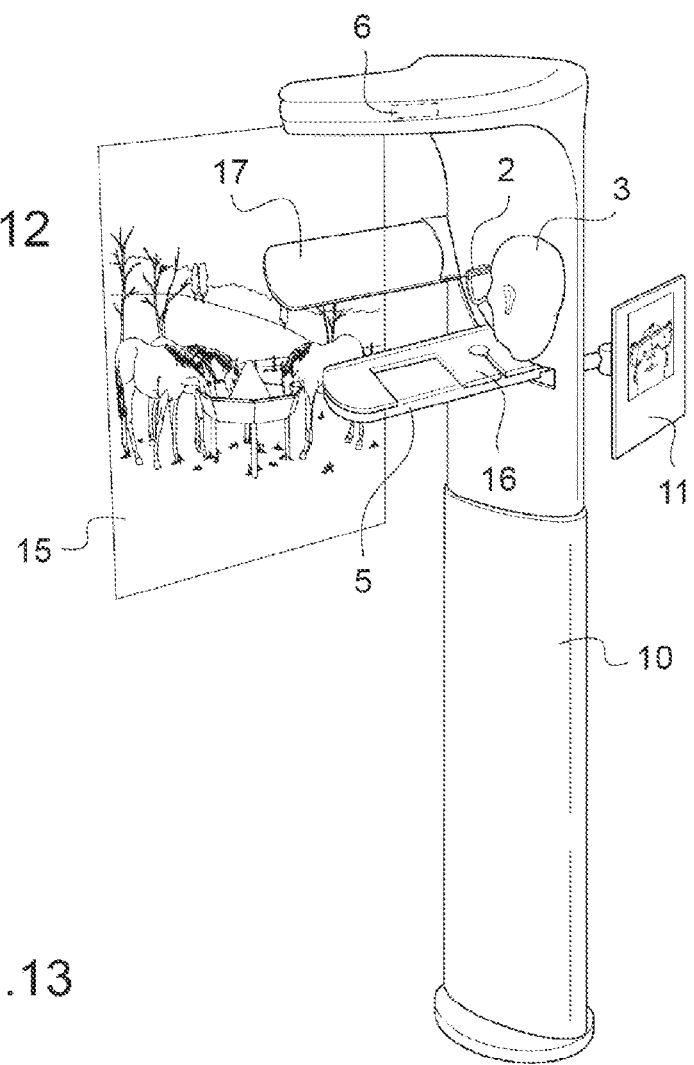
Figure 13:
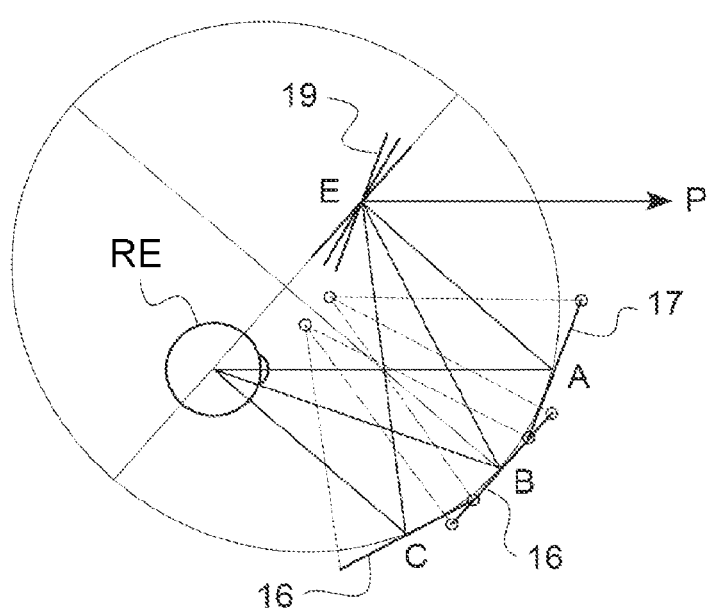

FIG. 5 schematically represents the same apparatus as in FIG. 4, under near vision measurement conditions;

FIG. 6A schematically represents a lighting system and an image capture system allowing the simultaneous measurement of the refraction and of the frame-fitting parameters according to a first variant; FIG. 6B schematically represents a lighting system and an image capture system according to a second variant;

FIG. 7A schematically represents a perspective view of a column-wise measuring device positioned facing a wearer equipped with a clip mounted on a spectacles frame; FIG. 7B represents the device of FIG. 7A with a partial section showing the lighting and image capture system;

FIG. 8A schematically represents a rear three-quarter view of a column-wise measuring device positioned facing a wearer equipped with a fixed clip on a spectacles frame under far vision measurement conditions; FIG. 8B schematically represents a view, taken from the imaging camera in far vision, of the wearer equipped with a clip; FIG. 8C represents the device of FIG. 8A showing the lighting and image capture system;

FIG. 9 schematically represents a side view of a measuring device according to a first embodiment, under far vision measurement conditions;

FIG. 10 schematically represents a side view of a measuring device according to the first embodiment, under near vision measurement conditions;

FIG. 11A schematically represents an overall view of a column-wise measuring device of FIGS. 9 and 10, positioned facing a wearer equipped with a clip mounted on a spectacles frame under near vision measurement conditions;

FIG. 11B schematically represents a near vision reading tablet; FIG. 11C schematically represents a view, taken from the imaging camera in near vision, of the wearer equipped with a clip;

FIG. 12 schematically represents an overall view of a column-wise measuring device according to another embodiment;

FIG. 13 schematically represents the operation of the optical return system of the device of FIG. 12.

In the present document, the expression "visual behavior" is intended to mean a set of parameters comprising the vision distance, or proximity of a target, the position of the pupils, the orientation of the axis of the gaze, the vergence of the gaze, the lowering of the gaze with respect to a horizontal line, as well as the body posture and the head posture of the subject.

In particular, a visual behavior in far vision (FV) is defined, in which the target for stimulating the gaze is disposed at the height of the eyes, the individual looking straight in front of himself, the head being straight, the stimulation target being at a distance from the individual such that it exhibits a proximity of less than two diopters. A visual behavior in near vision (NV) is also defined, in which a target for stimulating the gaze is disposed in such a way that the head of the individual is inclined and/or his gaze is lowered by an angle lying between −10 and −50 degrees with respect to a horizontal line, the target being at a distance such as it has a proximity of between 1 and 5 diopters.

Device

Figure 1:
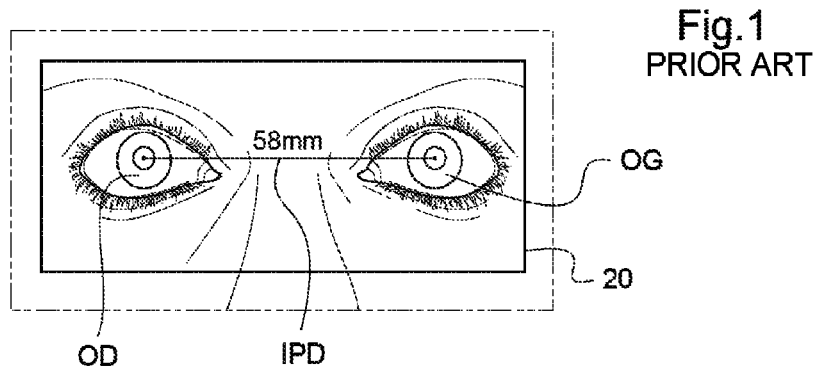
FIG. 1 is a view of a graphical interface of an ocular refraction measurement apparatus according to the prior art.
Figure 2:
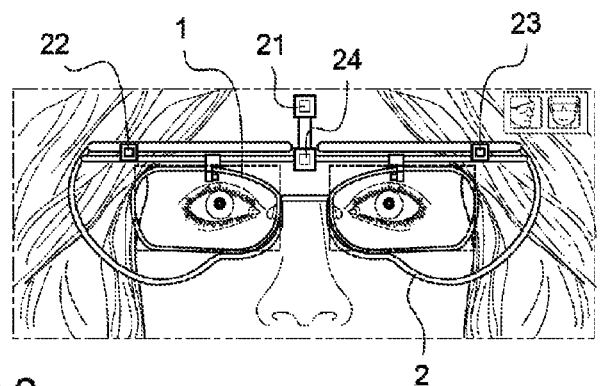
FIG. 2 is a view of a graphical interface of an apparatus for measuring frame-fitting parameters according to the prior art.
Figure 3:
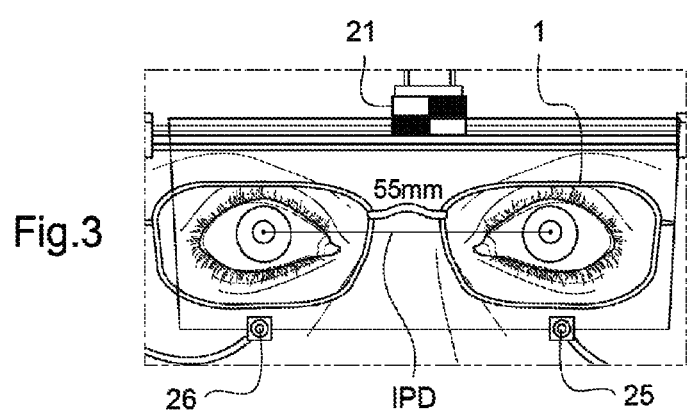
FIG. 3 illustrates a view of a graphical interface of a measurement apparatus according to a preferred embodiment of the invention.

In FIG. 3, an exemplary graphical interface of a combined measuring device has been represented. In this example, a subject wears a spectacles frame 1 on which is fixed a clip 2 furnished with markers 21, 25, 26. There exist various types of markers: black and white markers and gray level markers so as to make it possible to tailor the illumination, especially in the visible. The measuring device acquires an image, or a sequence of images, of the individual wearing the frame and deduces therefrom a combined measurement of the ocular refraction parameters of the two eyes and of at least one geometrico-morphological parameter (for example a frame-fitting parameter) in a determined visual behavior, identical for the two types of measurement. Accordingly, the apparatus uses a device combining a lighting system necessary for photorefraction and an image detector making it possible to measure the refraction of the two eyes as well as the frame-fitting parameters. The image detector collects not only an image of the wearer's face but also a signal by refraction of the lighting beam on the wearer's eyes.

FIG. 4 is a schematic view of a measuring device according to a first embodiment. The subject 3 wears a spectacles frame equipped with a clip 2 bearing markers such as for example represented in FIG. 3. The measuring device 4 comprises a target for stimulating the gaze so as to stimulate the gaze of the subject in a determined visual behavior. In the example represented in FIG. 4, the visual behavior corresponds to far vision, the target having a proximity value P1 of less than two diopters, the axis of the gaze is horizontal and the vision is binocular. The measuring device 4 also comprises a lighting system for generating a lighting beam 34. In an advantageous manner, the lighting system comprises at least one infrared source for generating an infrared lighting beam so as to illuminate the subject's eyes without dazzling him. The lighting beam 34 has sufficient divergence to also illuminate at least one part of the subject's face around the eyes. For example, the lighting system comprises a set of infrared light-emitting diodes (LED). In an advantageous manner, the clip 2 comprises retro-reflector markers operating in the infrared region. The measuring device 4 also comprises an image capture system able to form an image of at least one part of the face of the subject 3 wearing the frame 1. The image capture system advantageously comprises an optical system able to form an image of the face of the subject in the plane of an image sensor. Advantageously, the lighting beam 34 is centered on the optical axis 36 of the image capture system. In a preferred manner, the optical image capture system is able to form an infrared image and the image capture system comprises an infrared camera. By refraction on the ocular media of the eye, the lighting beam 34 forms an ocular refraction signal. By reflection and/or scattering on the face and on the retro-reflector markers, the lighting beam 34 also forms a retro-reflection and/or retro-scattering beam directed toward the image capture system. The image capture system receives an image of the face of the wearer, of the frame and of the retro-reflector markers of the clip. The subject still being in the same posture, the image capture system also receives a signal representative of the beam from ocular refraction on the eyes of the subject. A computer makes it possible to extract from the detected image at least one ocular refraction parameter and at least one frame-fitting parameter. The image of the subject being taken in a determined visual behavior, the measurements of ocular refraction and of frame-fitting parameters are thus carried out for one and the same visual behavior of the subject (in the example represented: head straight, gaze horizontal, proximity value P1 of the target less than two diopters).

FIG. 5 is a schematic view of a measuring device in a measurement configuration for another visual behavior of the subject, for example a behavior in near vision. The measuring device is analogous to that described in relation with FIG. 4, the subject 3 wearing a frame 1 equipped with a clip 2. The device of FIG. 5 furthermore comprises, for NV, a target 5 having a proximity value P2 of between two and five diopters and disposed so as to stimulate a behavior in near vision, with an axis of the gaze inclined by an angle of between −10 and −50 degrees with respect to a horizontal line, in vision is binocular. The target 5 can take the form of a tablet. The lighting system generates a lighting beam 134 directed toward the eyes and at least one part of the subject's face so as to simultaneously illuminate both eyes, the frame and the clip. The lighting beam 134 is directed directly toward the eyes of the subject or by an optical return system along the inclined optical axis 136. The image capture system receives an image or a sequence of images of the face of the wearer and also a signal representative of the beam from ocular refraction on the eyes of the subject for the visual behavior in NV. In a manner similar to the measurements in FV, a computer makes it possible to extract from the detected image at least one ocular refraction parameter and at least one frame-fitting parameter for the visual behavior in NV (in the example represented: head and/or gaze inclined with respect to the horizontal, proximity value P2 of the target of between two and five diopters).

On the basis of the measurements in FV and in NV, the computer can deduce therefrom a differentiated measurement of the refraction parameters between FV and NV. For example, it is thus possible to obtain a measurement of astigmatism differentiated between FV and NV.

FIG. 6A schematically represents a detail of the measurement system 4 comprising a lighting system 8 consisting of infrared LEDs 18 disposed on an annulus in concentric circles around the axis of the image capture system. The return image beams pass through the central aperture of the annulus. The image capture system comprises an objective 7, preferably operating at least in the infrared, and a camera 6, preferably infrared also. In the example represented, the LEDs 18 are disposed in annular sectors around the axis of the objective 7 of the camera 6. The LEDs 18 are switched on according to a predetermined sequence so as to form a signal making it possible to perform a determination of the ocular refraction.

Preferably, the camera 6 records a sequence of images in a manner synchronous with a switch-on sequence for various LEDs 18.

Preferably, the Leds 18 are disposed as six sectors (at least three sectors), each sector being driven independently so as to measure the refraction in the meridian of the two eyes corresponding to this sector. The measurement of the various refraction values for each meridian then makes it possible to determine the complete refraction of the eye (the sphere, the cylinder, the cylinder axis).

A computer makes it possible, on the basis of the sequence of images recorded, to determine an objective ocular refraction measurement.

For the measurement of the frame-fitting parameters, preferably the whole set of sectors is switched on so as to illuminate the face in a homogeneous manner and to increase the quantity of light received.

A preferential switch-on sequence consists in switching on the whole set of sectors while the wearer is being placed in position, doing so in order to best view his face, to carry out a first image capture, and then to switch on each sector independently and to capture an image for each sector.

The complete sequence or the independent switching on of the various sectors can be carried out multiple times, so as to measure the refraction continuously, or to carry out an averaging of the values obtained in respect of the refraction parameters or of the frame-fitting parameters.

Alternatively, it is also possible to envisage using just a single sector for the whole set of measurements, and in this case a limited refraction measurement is carried out (measurement of refractive power on the axis of the segment). In this case, the sequence consists merely of a single image and from this image are deduced at one and the same time the frame-fitting and refraction parameters (degraded mode).

FIG. 6B represents a measurement system 4 according to a variant furthermore comprising a visible lighting device 28. Advantageously, the lighting system using infrared LEDs 18 is implemented for photorefraction measurements and the visible lighting system 28 is activated so as to generate lighting in the visible for the frame-fitting measurements and to stimulate the master eye.

A difficulty with unconstrained measurement is the positioning of the wearer facing the camera for the measurement in NV. Indeed in the case of a stimulus in NV, the wearer has a tendency to position the NV target (for example a tablet 5) toward his master eye with the risk of exiting the field of the camera. Accordingly, three visible LEDs 28 are employed. The central LED switches on and the wearer is requested to gaze at the image 128 of the central LED 28 through a circle 50 of the tablet 5 (FIG. 11B). The computer deduces the master eye therefrom. Next as a function of the master eye, one of the two exterior Leds 28 is switched on to force the wearer to reposition himself facing the measurement system.

The visible lighting 28 and infrared 8 sources can be switched on simultaneously or sequentially. In FIG. 6B, the image capture system furthermore comprises a filter wheel 9 disposed between the objective 7 and the infrared sensor 6. The filter wheel 9 comprises various filters such as for example an infrared filter, red-green-blue (RGB) filters so as to select a spectral image in the visible or the infrared respectively.

In FIGS. 7 to 8 is represented a first embodiment of a photorefraction system integrated into a "Visioffice" type measurement taking column. The column 10 supports all the elements of the measuring device, apart from the clip 2 fixed on the frame. The column 10 supports in particular a viewing screen 11 which makes it possible at one and the same time to control the alignment of the measurement head and to display the results. The viewing screen 11 is linked to a computer which collects all the data and processes these data. In an advantageous manner, the computer is integrated into the column 10. The column 10 comprises a splitter plate 13 which is at least partially reflecting in the visible and transparent in the infrared. The splitter plate 13 can also be partially transparent in the visible. The splitter plate 13 acts as mirror and mask as regard the lighting system as well as the image capture system. FIGS. 7B and 8C show in partial section the position of the lighting system and of the image capture system which are aligned facing a wearer in a posture in FV.

In FIGS. 7B and 8C it is observed that the column 10 comprises a guide rail 12. Advantageously, the lighting and image capture system is mounted on a translation carriage that is mobile along the guide rail. Preferably, the displacement of the carriage is motorized. The carriage is displaced so as to align substantially the axis of the camera with the axis of the gaze of the wearer in far vision. During this adjustment, the camera acquires images. The viewing screen 11 makes it possible to control the position of the camera with respect to the wearer's face. The column is constructed in such a way that the axis of the camera is perpendicular to the surface of the mirror 13. To simulate far vision, the wearer can for example gaze at his reflection 33 in the semi-transparent mirror 13 (cf FIG. 8A). The wearer is then placed facing the axis of the camera. The height of the image capture system is tailored so as to adapt to the size of the wearers during an FV measurement while standing. The wearer is equipped with his spectacles frame to which is fastened a clip 2 furnished with markers 21, 22, 23, 24, 25, 26, 27 making it possible to locate the spectacles frame in space and with respect to the pupils (cf FIGS. 8B-8C).

FIG. 9 schematically represents the configuration for a measurement in FV of a column device such as that represented in FIGS. 7 and 8. A camera 6 is furnished with an objective 7 and with a filter wheel 9. A lighting system comprises on the one hand infrared LEDs disposed around the axis of the camera 6 and on the other hand a visible lighting system 28 disposed just below the camera 6. As described in relation with FIG. 6B, the visible lighting system 28 makes it possible to manage the wearer's master eye. The individual wears a spectacles frame 1 equipped with a clip 2. In FIG. 9, the individual is in a far posture, the axis of his gaze being horizontal. A reference (OX, OZ) tied to the individual's head is defined. The X axis passes through the center of rotation (CRE) of the eye and through the wearers porion O, the porion being the highest skull point of the auditory canal, which corresponds to the tragion of the ear, that is to say the highest point of the tragus of the ear. The Z axis passes through the point O and is perpendicular to the X axis. In far vision, the head is straight (the X axis is horizontal and the Z axis vertical) and the gaze is straight ahead, the axis of the gaze being parallel to the horizontal X axis. The axis 36 of the optical image capture system is also horizontal. The device comprises means for measuring the distance D1 between the individual's face and the image capture system. For example, it is possible to use the markers of the clip 2 to measure the distance D1. A check is carried out to verify that the distance D1 is greater than a minimum distance, so that the proximity of the far vision target (for example the reflection 33 in the mirror) is less than two diopters.

Moreover, the measurement of the distance D1 makes it possible to determine the scale factor (size of a pixel in the object space) and thus to precisely measure the frame-fitting parameters (DLE,CRE,PD,H). This distance D1 also makes it possible to ensure that the individual is positioned at a distance compatible with quality measurements, for example that he is in the focusing plane of the image acquisition system. Finally, this distance is used to improve the precision of the refraction measurement, in particular for strong refractions.

It is thus possible to experimentally compare a pre-established law of variation of the refraction with respect to the refraction measured as a function of distance and knowing the distance for the individual and his measured refraction, it is thus possible to correct the distance error in the refraction.

FIG. 10 schematically represents the configuration for a measurement in NV of a column device. In the posture in NV, the Z axis is inclined with respect to a vertical axis V by an angle beta, also called the head angle. The axis of the gaze is inclined with respect to the X axis by an angle gamma, also called the angle of lowering of the gaze. In FIG. 10, the individual is in the near posture, the axis of his gaze being lowered by an angle of about 60° (composed for example of a head angle beta of 25 degrees with respect to the vertical and of an angle of lowering of the gaze gamma of 35 degrees with respect to the head). In the case of close vision, it is possible to use a tablet 5 on which are inscribed patterns forming a target for near vision. The distance D2 determines the proximity of the near vision target. The tablet 5 also makes it possible to measure the wearer's visual behavior (lowering of the gaze, posture of the head, reading distance, etc.). Accordingly the tablet 5 is equipped with a return mirror 14 disposed between the tablet 5 and the lighting and image capture system. The displacement carriage makes it possible to modify the height of the measurement head. The axis 36 of the camera remains horizontal. The plane return mirror 14 makes it possible to deviate the axis 36 of the camera and of the lighting system onto an axis 136 aligned with the axis of the gaze of the individual in near vision (FIG. 10).

The adjustment of the orientation of the tablet 5 is carried out by the individual. For example, the displacement carriage positions the axis of the camera/lighting system at a lower height, corresponding to the height of the tablet when the individual is in the reading position. The individual then orients the tablet so as to perceive (the tablet is transparent at the periphery for example) the camera/system axis at the center of the tablet, and then observes without shifting the orientation a silk-screen-printed pattern 50, represented for example in FIG. 11B, on the tablet 5.

FIG. 11A represents an overall view of the column-wise measuring device furnished with a tablet 5 for measurement in NV. FIG. 11 B represents in greater detail the visible lighting system 28, the viewing and control screen, the tablet 5 as well as the positions of the clip 2, of the right eye RE and of the left eye LE of the wearer. FIG. 110 represents an image taken by the camera facing the return mirror 14. An image is observed of the face of the individual wearing a frame and a clip. A guide framework allows the subject to refine his positioning laterally (for example in relation to the central axis 55 silk-screen-printed on the mirror 14) and/or in terms of distance (D2) with respect to the measuring device. The markers 41, 42, 43 make it possible to control the centering and the orientation of the tablet 5 with respect to the axis 36 of the image capture system.

In FIG. 12 is represented another embodiment of a column-wise measuring device. The device comprises a column 10 which integrates a measurement system, a computer and a graphical interface 11 for control and display of measurement results. In an advantageous manner, the measurement system comprising the camera 6 and the lighting system is situated in the upper part of the column. The measurement system is oriented downwards, directed toward a near vision target 5. Advantageously, according to this embodiment, the measurement system is fixed in height and orientable, for example via a small return mirror, whatever the visual behavior and whatever the size of the individual. The device of FIG. 12 furthermore comprises a splitter plate that can move between at least one position 16 corresponding to a visual behavior in NV and another position 17 corresponding to a visual behavior in FV. In this figure, the top plate 17 corresponding to far vision is fixed and it is possible for the bottom plate 16 to move angularly so as to manage several angles of lowering of the gaze. The position of an eye RE of the subject during the measurements has been represented schematically. The subject wears a frame equipped with a clip. The splitter plate is placed in a first measurement position 17 for FV. Advantageously, the height of the column can be tailored as a function of the size of the subject. In a first visual behavior (FV), the subject is requested to observe a particular point on a target 15 having a proximity of less than two diopters. Preferably, the splitter plate 17 is transparent in the visible region and reflecting in the infrared region. The subject can therefore observe the target 15 in FV by transparency through the splitter plate in position 17. The splitter plate 17 is oriented in such a way that the image capture system 6, situated in the upper part, is able to carry out an image acquisition of the wearer (see FIG. 12). For the measurement in NV, the subject is requested to observe another target 5 situated behind the splitter plate 16. The target 5 has a proximity of between two and five diopters. An orientable mirror makes it possible to align the optical axis of the image capture system with the sighting axis of the subject. The splitter plate 16 is angularly orientable, jointly with the target 5 so as to simulate various angles of lowering of the gaze in near vision. The image capture system follows the movements of the splitter plate and of the target so as to maintain the alignment between the optical axis of the image capture system and the sighting axis of the subject.

In FIG. 13 is represented an exemplary optical device making it possible to direct the image beam toward a fixed camera. The fixed position A of the splitter plate 17 and two separate positions B and C of the splitter plate 16 have been represented schematically as a side view. An orientable mirror 19 makes it possible to return the optical measurement axis in a constant direction defined by the straight line EP depending on whether the splitter plate 17 is used in position A or respectively the splitter plate 16 in position B or C. The optical measurement axis is thus aligned with the optical sighting axis, whatever the angle of lowering of the gaze.

Preferably, the device of the invention makes it possible to stimulate various vision behaviors of the individual wearing spectacles for example by using several targets for stimulating the gaze or by modifying the position and the proximity value of a target, the wearer gazing at each target in a natural position. Jointly, an image capture system makes it possible to perform measurements under several vision conditions, such as far vision behavior and/or near vision behavior. Accordingly, the apparatus uses an imaging system combining the lighting necessary for photorefraction and the image capture making it possible to measure the refraction of both eyes as well as the frame-fitting parameters.

The advantages of such a solution are:
the combining (simultaneously or sequentially) of two measurements that may be lengthy and generally performed at different locations. The measurement time is reduced and the wearer does not have to move, everything is centralized on the same instrument. The device does not induce any proximal accommodation since the field is free ahead of the subject (there is no frontal rest or chinstrap).
The refraction is performed within the framework of a natural behavior of the wearer (head posture, binocular vision, personal reading distance, etc.)
Screening for various disorders of the vision such as cataracts, keratoconus or the problems of phoria.

The invention claimed is:

1. A device for measuring objective ocular refraction and at least one geometrico-morphological parameter of an individual, said device comprising:
at least one first target for stimulating the gaze having a center disposed in a first position so as to stimulate the gaze of the individual in a first posture associated with a first proximity value P1 and a first sighting axis,
a lighting system comprising at least one luminous source, the lighting system being able to generate at least one lighting beam directed toward the eyes of the individual in the first posture,
an image capture system,
a computer,
characterized in that the measuring device furthermore comprises:
at least one second target for stimulating the gaze having a center disposed in a second position so as to stimulate the gaze of the individual in a second posture associated with a second proximity value and a second sighting axis,
an optical return system disposed between on the one hand the second target for stimulating the gaze and on the other hand the image capture system and the lighting system, the optical return system being adapted, in a determined orientation, to return the lighting beam toward the eyes of the individual looking at the second target in a second posture, and in that
the image capture system is adapted for obtaining a first image acquisition comprising a part of the face surrounding the eyes of the individual in the first posture, the image capture system being adapted for obtaining via the optical return system a second image acquisition comprising a part of the face surrounding the eyes of the individual in the second posture, and
the computer is adapted for receiving and extracting from said at least one first image acquisition on the one hand a first measurement of at least one geometrico-morphological parameter of the individual in the first posture and on the other hand a first measurement of objective ocular refraction by refraction of the lighting beam on the eyes of the individual in the first posture and the computer being adapted for extracting from said second image acquisition on the one hand a second measurement of a geometrico-morphological parameter of the individual in the second posture and on the other hand a second measurement of objective ocular refraction by refraction of the lighting beam on the eyes of the individual in the second posture.

2. The measuring device as claimed in claim 1, in which said at least one geometrico-morphological parameter consists of at least one frame-fitting parameter for an individual wearing a spectacles frame.

3. The measuring device as claimed in claim 2, in which the lighting system generating a lighting beam and the image capture system defining an optical axis, the lighting system and the image capture system are disposed with respect to one another in such a way that the lighting beam is centered on the optical axis of the image capture system.

4. The measuring device as claimed in claim 2, furthermore comprising a clip furnished with markers which is intended to be mounted on a spectacles frame and in which the image capture system exhibits an image field adapted for simultaneously detecting an image comprising a part of the face surrounding the eyes of the individual wearing the spectacles frame and an image of the markers of the clip mounted on the spectacles frame.

5. The measuring device as claimed in claim 2, in which the lighting system comprises at least one infrared luminous source and in which the image capture system comprises an infrared camera.

6. The measuring device as claimed in claim 2 comprising means of displacement and/or orientation of the image capture system which are able to align the optical axis of the image capture system with the first sighting axis associated with the first target and/or respectively to align the optical axis of the image capture system with the second ocular sighting axis associated with the second target.

7. The measuring device as claimed in claim 2, comprising a column supporting the lighting system, the image capture system, the computer, at least one first target and a viewing screen.

8. The measuring device as claimed in claim 1, in which the lighting system generating a lighting beam and the image capture system defining an optical axis, the lighting system and the image capture system are disposed with respect to one another in such a way that the lighting beam is centered on the optical axis of the image capture system.

9. The measuring device as claimed in claim 1, furthermore comprising means for measuring the distance between said image capture system and the individual in the first posture and/or in the second posture, said distance measuring means being selected from among: a telemeter, an image processing system based on the image quality, an image processing system based on a measurement of markers of a clip fixed to a spectacles frame, a calibration system or a system for measuring distance by ultrasounds.

10. The measuring device as claimed in claim 1, furthermore comprising a clip furnished with markers which is intended to be mounted on a spectacles frame and in which the image capture system exhibits an image field adapted for simultaneously detecting an image comprising a part of the face surrounding the eyes of the individual wearing the spectacles frame and an image of the markers of the clip mounted on the spectacles frame.

11. The measuring device as claimed in claim 1, in which the lighting system comprises at least one infrared luminous source and in which the image capture system comprises an infrared camera.

12. The measuring device as claimed in claim 11 comprising means of displacement and/or orientation of the image capture system which are able to align the optical axis of the image capture system with the first sighting axis associated with the first target and/or respectively to align the optical axis of the image capture system with the second ocular sighting axis associated with the second target.

13. The measuring device as claimed in claim 11, comprising a column supporting the lighting system, the image capture system, the computer, at least one first target and a viewing screen.

14. The measuring device as claimed in claim 1 comprising means of displacement and/or orientation of the image capture system which are able to align the optical axis of the image capture system with the first sighting axis associated with the first target and/or respectively to align the optical axis of the image capture system with the second ocular sighting axis associated with the second target.

15. The measuring device as claimed in claim 1, comprising means of displacement and/or of orientation of the optical return system which are able to return the optical axis of the image capture system to the first ocular sighting axis associated with the first target and respectively to the second ocular sighting axis associated with the second target.

16. The measuring device as claimed in claim 1, comprising a column supporting the lighting system, the image capture system, the computer, at least one first target and a viewing screen.

17. A method for measuring objective ocular refraction and at least one geometrico-morphological parameter of an individual, said method comprising the following steps:
    activating at least one first target for stimulating the gaze so as to stimulate the gaze of the individual in a first posture associated with a first proximity value and a first sighting axis,
    generating at least one lighting beam directed toward the eyes of the individual in the first posture,
    obtaining at least one first image acquisition of a part of the face surrounding the eyes of the individual,
    computing on the basis of said at least one first image acquisition on the one hand a first measurement of at least one geometrico-morphological parameter of the individual in the first posture and on the other hand a first measurement of objective ocular refraction of the individual in the first posture,
    activating at least one second target for stimulating the gaze so as to stimulate the gaze of the individual in a second posture associated with a second proximity value and a second sighting axis,
    generating at least one lighting beam directed toward the eyes of the individual in the second posture,
    obtaining at least one second image acquisition of a part of the face surrounding the eyes of the individual,
    computing on the basis of said at least one second image acquisition on the one hand a second measurement of at least one geometrico-morphological parameter of the individual in the second posture and on the other hand a second measurement of objective ocular refraction of the individual in the second posture.

18. The measuring method as claimed in claim 17, in which said at least one geometrico-morphological parameter consists of at least one frame-fitting parameter for an individual wearing a spectacles frame, the frame-fitting parameter being selected from among the interpupillary distances, the lens-eye distance, the position of the center of rotation of the eye, the height of the eyes in relation to the lower edge of the frame.

19. The measuring method as claimed in claim 17, in which the first measurement of at least one geometrico-morphological parameter and the first measurement of objective ocular refraction of the individual in the first posture are sequential or simultaneous measurements.

20. The measuring method as claimed in claim 17, comprising an additional step of controlling the first posture and/or the second posture in such a way that the first sighting axis associated with the first posture and/or respectively the second sighting axis associated with the second posture, is included in a cone centered on the optical axis of the image capture system, said cone having a vertex angle of less than or equal to ten degrees.

21. The measuring method as claimed in claim 17, furthermore comprising a step of measuring an angle of lowering of the gaze of the individual.

22. The measuring method as claimed in claim 17, furthermore comprising a step of measuring at least one physiological parameter of vision of the individual wearing a spectacles frame in the first and/or second posture, the physiological vision parameter being representative of strabismus, keratoconus or of cataracts or of behavioral parameters of the individual.

23. The measuring method as claimed in claim 17, in which the individual wearing a spectacles frame equipped with lenses, the method comprises an additional step of correcting the ocular refraction measurement on the basis of at least one of the following values: the power correction value of the lenses or the value of the transmission coefficient of the lenses.

* * * * *